United States Patent [19]

Takase et al.

[11] Patent Number: 5,393,889
[45] Date of Patent: Feb. 28, 1995

[54] WATER SOLUBLE BIS-DIOXOPIPERAZINE DERIVATIVES

[75] Inventors: Muneaki Takase, Tokyo; Toshiharu Narita, Higashimurayama; Toshihiko Komatsu, Kawagoe, all of Japan

[73] Assignee: Zenyaku Kogyo Kabushiki Kaisha, Tokyo, Japan

[21] Appl. No.: 835,927

[22] PCT Filed: Jul. 3, 1991

[86] PCT No.: PCT/JP91/00894

§ 371 Date: Mar. 2, 1992

§ 102(e) Date: Mar. 2, 1992

[87] PCT Pub. No.: WO92/00971

PCT Pub. Date: Jan. 23, 1992

[30] Foreign Application Priority Data

Jul. 4, 1990 [JP] Japan .................. 2-176672

[51] Int. Cl.$^6$ .............. C07D 241/08; C07D 403/14; C07D 417/14
[52] U.S. Cl. .................................... 544/357
[58] Field of Search .................. 544/357; 514/252

[56] References Cited

U.S. PATENT DOCUMENTS

| | | | |
|---|---|---|---|
| 4,650,799 | 3/1987 | Cai et al. | 514/255 |
| 4,737,497 | 4/1988 | Ren | 514/232.2 |
| 4,868,303 | 9/1989 | Takase et al. | 544/357 |
| 4,877,803 | 10/1989 | Cai et al. | 514/227.8 |

FOREIGN PATENT DOCUMENTS 61-152660  7/1986  Japan .
62-135472  6/1987  Japan .
 1-279875 11/1989  Japan .

OTHER PUBLICATIONS

Derwent Abstract for JP 62-135472 (Jun. 18, 1987).
Derwent Abstract for JP 61-152660 (Jul. 11, 1986).
Derwent Abstract for JP 1-279875 (Nov. 10, 1989).
Sai et al, Chemical Abstracts, vol. 106, No. 18614 (1987) (Abstract for JP 61-152660, Jul. 11, 1986).

14th International Congress of Chemotherapy, p. 324, Jun. 1985, Abstract p-18-34, Cai et al.
8th International Congress of Pharmacology, p. 441, Jul. 1981, Abstract 722, Zhang et al.

*Primary Examiner*—Emily Bernhardt
*Attorney, Agent, or Firm*—Oblon, Spivak, McClelland, Maier & Neustadt

[57] ABSTRACT

A pharmaceutically-acceptable acid addition salt of a bis-dioxopiperazine derivative of the formula (I):

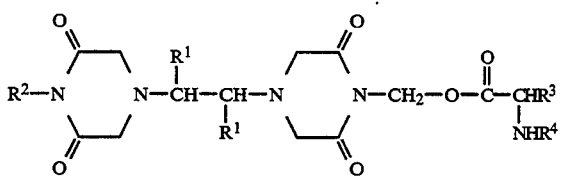

which derivative exhibits anti-tumor potency and is water-soluble, wherein $R^1$ is a $C_{1-6}$ alkyl group, $R^2$ represents a hydrogen atom or:

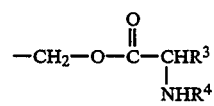

$R^3$ represents a hydrogen atom, a $C_{1-6}$ alkyl group or $(CH_2)_nA$, wherein A respresents carboxyl, benzyloxycarbonyl, mercapto, amino, benzyloxycarbonylamino or:

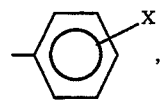

and n is an integer of 1, 2, 3 or 4, and $R^4$ represents a hydrogen atom or is coupled with $R^3$ into a 5-membered ring, which may contain one sulfur atom as an additional ring heteroatom.

16 Claims, No Drawings

WATER SOLUBLE BIS-DIOXOPIPERAZINE DERIVATIVES

TECHNICAL FIELD

Compounds of the present invention are acid addition salts of bis-dioxopiperazine derivatives represented by the formula (I)

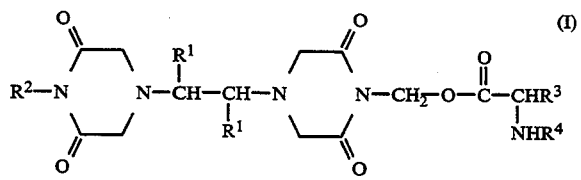

wherein $R^1$ represents a $C_{1-6}$ alkyl group, $R^2$ represents a hydrogen atom or a group of

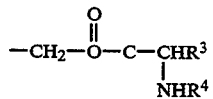

$R^3$ represents a hydrogen atom, a $C_{1-6}$ alkyl group or a group of —$(CH_2)_n$—A in which A represents a carboxyl group, a benzyloxycarbonyl group, a mercapto group, an amino group, a benzyloxycarbonylamino group or a group of

in which X represents a hydrogen atom, a trifluoromethyl group, a hydroxy group, an acetoxy group or a benzyloxy group, and n is an integer and is 1, 2, 3 or 4, and $R^4$ represents a hydrogen atom or is coupled with $R^3$ into a 5-membered ring which may contain a sulfur atom.

Synthetic intermediates of the compounds of the present invention are water soluble bis-dioxopiperazine derivatives having antitumor activity represented by the formula (II)

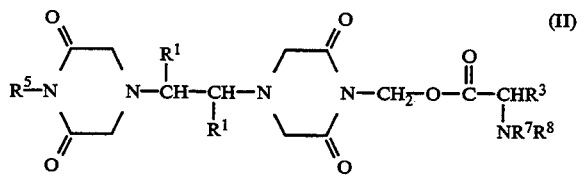

where in $R^1$ is as defined above, $R^5$ represents a hydrogen atom or a group of

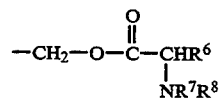

$R^6$ represents a hydrogen atom, a $C_{1-6}$ alkyl group or a group of —$(CH_2)_n$—A' in which A' represents a carboxyl group, a benzyloxycarbonyl group, a benzylthio group which may be substituted by a $C_{1-6}$ alkoxy group, a benzyloxycarbonylamino group or a group of

in which X represents a hydrogen atom, trifluoromethyl group, a hydroxyl group, an acetoxy group or benzyloxy group, and n is an integer and is 1, 2, 3 or 4, $R^7$ represents a hydrogen atom or is coupled with $R^6$ into a 5-membered ring which may contain a sulfur atom, $R^8$ represents a protective group for amino group.

BACKGROUND ART

Several kinds of bis-dioxopiperazine derivatives have been already reported. Among them, especially known as compounds having antitumor activity are 1,2-bis(4-morpholinomethyl-3,5-dioxopiperazin-1-yl)ethane (see Abstract, 8th International Congress of Pharmacology p441, 1981), dl-1,2-bis(4-morpholinomethyl-3,5-dioxopiperazin-1-yl)propane (see Japanese Patent Publication (Kokai) No. 190976/1984) and 1,2-bis(4-isobutoxycarbonyloxymethyl-3,5-dioxopiperazin-1-yl)ethane (see Abstract, 14th International Congress of Chemotherapy p324, 1985 and Japanese Patent Publication (Kokai) No. 97963/1985). Also known are the compounds described in the Japanese Patent Publication (Kokai) Nos. 152660/1986, 89668/1987, 281870/1987 and 279875/1989.

Though these compounds have excellent antitumor activity, water soluble salts thereof with retained activity cannot be formed so that route of administration and pharmaceutical form of the compounds are much limitative. Therefore, there has been a demand for a water soluble bis-dioxopiperazine derivative which may be expected to have wider clinical applicabilities.

Under these circumstances, we, the inventors carried out studies on novel bis-dioxopiperazine derivatives to find out that acid addition salts of the compounds represented by the formula (I) exhibit remarkably excellent antitumor activity, thus completing the present invention.

The terms used for definition of variables in the above-mentioned formulas (I) and (II) by which the compound of the present invention and synthetic intermediates thereof are respectively represented are defined and exemplified in the following.

The "$C_{1-6}$" refers to a group having 1 to 6 carbon atoms unless otherwise indicated.

The "$C_{1-6}$ alkyl group" refers to a straight- or branched-chain alkyl group such as methyl, ethyl, n-propyl, isopropyl, n-butyl, iso-butyl, tert-butyl, n-pentyl, n-hexyl or the like. Preferably, methyl is used for $R^1$.

The "$C_{1-6}$ alkoxy group" refers to a straight-or branched-chain alkoxy group such as methoxy, ethoxy, n-propoxy, isopropoxy, n-butoxy, isobutoxy, tert-butoxy, n-pentyloxy, n-hexyloxy or the like.

The "protective group for amino group" may be tert-butoxycarbonyl, benzyloxycarbonyl or the like.

The compound of the present invention are for example as follows:

2,3-bis[4-(2-aminoacetoxymethyl)-3,5-dioxopiperazin-1-yl]butane
2,3-bis[4-(2-aminopropionyloxymethyl)-3,5-dioxopiperazin-1-yl]butane
2,3-bis[4-(2-aminoisovaleryloxymethyl)-3,5-dioxopiperazin-1-yl]butane
2,3-bis[4-(2-amino-4-methylvaleryloxymethyl)-3,5-dioxopiperazin-1-yl]butane
2,3-bis[4-(2-amino-3,3-dimethylbutyryloxymethyl)-3,5-dioxopiperazin-1-yl]butane
2,3-bis[4-(2-amino-4,4-dimethylvaleryloxymethyl)-3,5-dioxopiperazin-1-yl]butane
2,3-bis[4-(2-amino-3-phenylpropionyloxymethyl)-3,5-dioxopiperazin-1-yl]butane
2,3-bis[4-(2-amino-6-phenylhexanoyloxymethyl)-3,5-dioxopiperazin-1-yl]-butane
2,3-bis[4-(2-amino-3-(p-trifluoromethylphenyl)propionyloxymethyl)-3,5-dioxopiperazin-1-yl]butane
2,3-bis[4-(2-amino-3-(p-hydroxyphenyl)propionyloxymethyl)-3,5-dioxopiperazin-1-yl]butane
2,3-bis[4-(2-amino-3-(p-benzyloxyphenyl)propionyloxymethyl)-3,5-dioxopiperazin-1-yl]butane
2,3-bis[4-(3-(p-acetoxyphenyl)-2-aminopropionyloxymethyl)-3,5-dioxopiperazin-1-yl]butane
2,3-bis[4-(2-amino-3-carboxypropionyloxymethyl)-3,5-dioxopiperazin-1-yl]butane
2,3-bis[4-(2-amino-4-carboxybutyryloxymethyl)-3,5-dioxopiperazin-1-yl]butane
2,3-bis[4-(2-amino-3-benzyloxycarbonylpropionyloxymethyl)-3,5-dioxopiperazin-1-yl]butane
2,3-bis[4-(2-amino-4-benzyloxycarbonylbutyryloxymethyl)-3,5-dioxopiperazin-1-yl]butane
2,3-bis[4-(2,4-diaminobutyryloxymethyl)-3,5-dioxopiperazin-1-yl]butane
2,3-bis[4-(2,6-diaminohexanoyloxymethyl)-3,5-dioxopiperazin-1-yl]butane
2,3-bis[4-(2-amino-3-mercaptopropionyloxymethyl)-3,5-dioxopiperazin-1-yl]butane
2,3-bis(4-pyrrolidinecarbonyloxymethyl-3,5-dioxopiperazin-1-yl)butane
2,3-bis(4-thiazolydinecarbonyloxymethyl-3,5-dioxopiperazin-1-yl)butane
2-[4-(2-aminoacetoxymethyl)-3,5-dioxopiperazin-1-yl]-3-(3,5-dioxopiperazin-1-yl)butane
2-[4-(2-aminopropionyloxymethyl)-3,5-dioxopiperazin-1-yl]-3-(3,5-dioxopiperazin-1-yl)butane
2-[4-(2-aminobutyryloxymethyl)-3,5-dioxopiperazin-1-yl]-3-(3,5-dioxopiperazin-1-yl)butane
2-[4-(2-aminovaleryloxymethyl)-3,5-dioxopiperazin-1-yl]-3-(3,5-dioxopiperazin-1-yl)butane
2-[4-(2-amino-4-methylvaleryloxymethyl)-3,5-dioxopiperazin-1-yl]-3-(3,5-dioxopiperazin-1-yl)butane
2-[4-(2-amino-3-(p-hydroxyphenyl)propionyloxymethyl)-3,5-dioxopiperazin-1-yl]-3-(3,5-dioxopiperazin-1-yl)butane
2-[4-(2-amino-3-carboxypropionyloxymethyl)-3,5-dioxopiperazin-1-yl]-3-(3,5-dioxopiperazin-1-yl)butane
2-[4-(2-amino-6-N-benzyloxycarbonylaminohexanoyloxymethyl)-3,5-dioxopiperazin-1-yl]-3-(3,5-dioxopiperazin-1-yl)butane
2-(4-pyrrolidinecarbonyloxymethyl-3,5-dioxopiperazin-1-yl)-3-(3,5-dioxopiperazin-1-yl)butane
2-(4-thiazolidinecarbonyloxymethyl-3,5-dioxopiperazin-1-yl)-3-(3,5-dioxopiperazin-1-yl)butane The compound (I) of the present invention has asymmetric carbon atoms in its molecules. It is to be understood that isomers due to such asymmetric carbon atom or combination of any of the isomers are included in the category of the compound (I). Especially, meso- or erythro-form is preferred.

Preferably, salts of the compounds of the present invention may be pharmaceutically acceptable salts such as hydrochloride, hydrobromide or trifluoroacetate.

A synthetic intermediate (II) of the present invention is a compound with a protecting group of an amino group which bonds $R^4$ of the compound (I) and is for example as follows:

2,3-bis[4-(2-N-tert-butoxycarbonylaminoacetoxymethyl)-3,5-dioxopiperazin-1-yl]butane
2,3-bis[4-(2-N-tert-butoxycarbonylaminopropionyloxymethyl)-3,5-dioxopiperazin-1-yl]butane
2,3-bis[4-(2-N-tert-butoxycarbonylaminoisovaleryloxymethyl)-3,5-dioxopiperazin-1-yl]butane
2,3-bis[4-(2-N-benzyloxycarbonylamino-4-methylvaleryloxymethyl)-3,5-dioxopiperazin-1-yl]butane
2,3-bis[4-(2-N-benzyloxycarbonylamino-3,3-dimethylbutyryloxymethyl)-3,5-dioxopiperazin-1-yl]butane
2,3-bis[4-(2-N-benzyloxycarbonylamino-4,4-dimethylvaleryloxymethyl)- 3,5-dioxopiperazin-1-yl]butane
2,3-bis[4-(2-N-tert-butoxycarbonylamino-3-phenylpropionyloxymethyl)-3,5-dioxopiperazin-1-yl]butane
2,3-bis[4-(2-N-tert-butoxycarbonylamino-6-phenylhexanoyloxymethyl)-3,5-dioxopiperazin-1-yl]butane
2,3-bis[4-(2-N-tert-butoxycarbonylamino-3-(p-trifluoromethylphenyl)propionyloxymethyl)-3,5-dioxopiperazin-1-yl]butane
2,3-bis[4-(2-N-tert-butoxycarbonylamino-3-(p-hydroxyphenyl)propionyloxymethyl)-3,5-dioxopiperazin-1-yl]butane
2,3-bis[4-(3-(p-benzyloxyphenyl)-2-N-tert-butoxycarbonylaminopropionyloxymethyl)-3,5-dioxopiperazin-1-yl]butane
2,3-bis[4-(3-(p-acetoxyphenyl)-2-N-tert-butoxycarbonylaminopropionyloxymethyl)-3,5-dioxopiperazin-1-yl]butane
2,3-bis[4-(2-N-tert-butoxycarbonylamino-3-carboxypropionyloxymethyl)-3,5-dioxopiperazin-1-yl]butane
2,3-bis[4-(2-N-tert-butoxycarbonylamino-4-carboxybutyryloxymethyl)-3,5-dioxopiperazin-1-yl]butane
2,3-bis[4-(3-benzyloxycarbonyl-2-N-tert-butoxycarbonylaminopropionyloxymethyl)-3,5-dioxopiperazin-1-yl]butane
2,3-bis[4-(4-benzyloxycarbonyl-2-N-tert-butoxycarbonylaminobutyryloxymethyl)-3,5-dioxopiperazin-1-yl]butane
2,3-bis[4-(6-N-benzyloxycarbonylamino-2-N-tert-butoxycarbonylaminohexanoyloxymethyl)-3,5-dioxopiperazin-1-yl]butane
2,3-bis[4-(4-N-benzyloxycarbonylamino-2-N-tert-butoxycarbonylaminobutyryloxymethyl)-3,5-dioxopiperazin-1-yl]butane
2,3-bis[4-(2-N-tert-butoxycarbonylamino-3-(p-methoxybenzylthio)propionyloxymethyl-3,5-dioxopiperazin-1-yl]butane
2,3-bis(4-N-tert-butoxycarbonylpyrrolidinecarbonyloxymethyl-3,5-dioxopiperazin-1-yl)butane
2,3-bis(4-N-tert-butoxycarbonylthiazolidinecarbonyloxymethyl-3,5-dioxopiperazin-1-yl)butane
2-[4-(2-N-tert-butoxycarbonylaminoacetoxymethyl)-3,5-dioxopiperazin-1-yl]-3-(3,5-dioxopiperazin-1-yl)butane 2-[4-(2-N-tert-butoxycarbonylaminopropionyloxymethyl)-3,5-dioxopiperazin-1-yl]-3-(3,5-dioxopiperazin-1-yl)butane 2-[4-(2-N-tert-butoxycarbonylaminobutyryloxymethyl)-3,5-dioxopiperazin-1-yl]-3-(3,5-dioxopiperazin-1-yl)butane 2-[4-(2-N-tert-butoxycarbonylaminovaleryloxymethyl)-3,5-dioxopiperazin-1-yl]-3-(3,5-dioxopiperazin-1-yl)butane 2-[4-(2-N-benzyloxycarbonylamino-4-methylvaleryloxymethyl)-3,5-dioxopiperazin-1-yl]-3-(3,5-dioxopiperazin-1-yl)butane 2-[4-(3-(p-benzyloxyphenyl)-2-N-tert-butoxycarbonylaminopropionyloxymethyl)-3,5-dioxopiperazin-1-yl]-3-(3,5-dioxopiperazin-1-yl)butane 2-[4-(3-benzyloxycarbonyl-2-N-tert-butoxycarbonylaminopropionyloxymethyl)-3,5-dioxopiperazin-1-yl]-3-(3,5-dioxopiperazin-1-yl)butane 2-[4-(2-N-tert-butoxycarbonylamino-3-carboxypropionyloxymethyl)-3,5-dioxopiperazin-1-yl]-3-(3,5-dioxopiperazin-1-yl)butane 2-[4-(6-N-benzyloxycarbonylamino-2-N-tert-butoxycarbonylaminohexanoyloxymethyl)-3,5-dioxopiperazin-1-yl]-3-(3,5-dioxopiperazin-1-yl)butane 2-(4-N-tert-butoxycarbonylpyrrolidinecarbonyloxymethyl-3,5-dioxopiperazin-1-yl)-3-(3,5-dioxopiperazin-1-yl)butane 2-(4-N-tert-butoxycarbonylthiazolidinecarbonyloxymethyl-3,5-dioxopiperazin-1-yl)-3-(3,5-dioxopiperazin-1-yl)butane The compounds (I) of the present invention may be prepared by the reaction of compound represented by the formula (III):

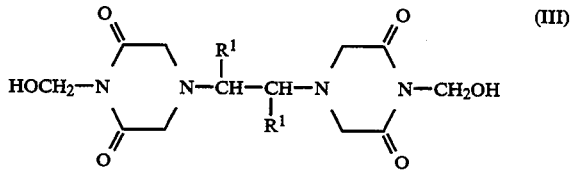

wherein $R^1$ is as defined above, with a compound represented by the forumula (IV):

wherein $R^6$, $R^7$ and $R^8$ are as defined above, (A) in the presence of a condensing agent to thereby readily afford the synthetic intermediate (II), followed by (B) removal of the protecting group $R^8$ of amino group by acidic hydrolysis or by catalytic reduction in the presence of an acid to thereby prepare the compound of the formula (I) or acid addition salt thereof.

In the reaction (A), the condensing agent may be, for example, 1-methyl-2-chloropyridinium iodide, dicyclohexylcarbodiimide or N,N'-carbonyldiimidazole. Preferably, methyl iodide is used as reaction accelerator in the case of N,N'-carbonyldiimidazole being a condensing agent used; and N,N-dimethylaminopyridine, in the case of the other condensing agents.

The reaction temperature may range from 0° to 30° C., and the reaction time may range from 16 to 48 hours depending on reaction temperature. In the above-mentioned reaction, 1.2 to 2.4 molar amount of the compound of the formula (IV) is used to one molar amount of the compound of the formula (III). As for the reaction solvent, an aprotic polar solvent such as N,N-dimethylformamide (DMF), pyridine, dichloromethane, chloroform, acetonitrile or their mixture may be used. In the above-mentioned reaction, the synthetic intermediates of the formula (II) with $R^5$ being hydrogen atom and the group of

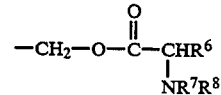

are concurrently generated, and are separated and purified according to ordinary method using silica gel column chromatography or the like.

Moreover, when the synthetic intermediates (II) contain a protective group or groups for phenolic hydroxyl, carboxyl, amino or mercapto group in addition to the protective group $R^8$, such protective group or groups can be removed together with the protective group $R^8$ by the reaction (B).

When the acidic hydrolysis is used in the reaction (B), the acid may be for example hydrogen chloride, hydrogen bromide or trifluoroacetic acid. The amount of the acid between 20 and 30 moles is used to one molar amount of the synthetic intermediate (II). The reaction temperature may range from 0° to 70° C. and the reaction time may range from 2 to 4 hours depending on reaction temperature. As for the reaction solvent, dioxane, acetic acid or the like may be used.

In the catalytic reduction, 10% palladium on carbon, 5% palladium on barium sulfate, platinum oxide or the like may be used as a catalyst; 10% palladium on carbon or platinum oxide is preferable. The acid used may be, for example, acetic or hydrochloric acid; and the reaction solvent may be methanol, ethanol, acetic acid, dioxane or the like. The reaction temperature may range from 0° to 70° C. and the reaction time may range from 1 to 24 hours depending on reaction temperature.

Thus obtained compound of the present invention or acid addition salt thereof may be isolated by usual manners such as extraction, concentration, filtration or recrystallization.

The compound of the formula (III) which is the starting material in the above-mentioned preparation can be readily obtained from the reaction of bis(3,5-dioxopiperazin-1-yl)alkane, which disclosed in British Patent No. 1234935, with formaldehyde.

The antitumor activity of the compounds of the formula (I) according to the present invention and prepared by the above-mentioned preparation process was verified by the below-mentioned tests.

Test samples in these tests were as follows:

Sample 1: Meso-2,3-bis[4-(2-aminoacetoxymethyl)-3,5-dioxopiperazin-1-yl]butane.hydrochloride Sample 2: Meso-2,3-bis[4-((S)-2-aminopropionyloxymethyl)-3,5-dioxopiperazin-1-yl]butane.hydrochloride Sample 3: Meso-2,3-bis[4-((S)-2-aminoisovaleryloxymethyl)-3,5-dioxopiperazin-1-yl]butane.hydrochloride Sample 4: Meso-2,3-bis[4-((S)-2-amino-4-methylvaleryloxymethyl)-3,5-dioxopiperazin-1-yl]butane.hydrochloride Sample 5: Meso-2,3-bis[4-((S)-2-amino-3-phenylpropionyloxymethyl)-3,5-dioxopiperazin-1-yl]butane.hydrochloride Sample 6: Meso-2,3-bis[4-((S)-2-amino-3-(p-trifluoromethylphenyl)propionyloxymethyl)-3,5-dioxopiperazin-1-yl]butane.hydrochloride Sample 7: Meso-2,3-bis[4-((S)-2-amino-3-(p-hydroxyphenyl)propionyloxymethyl)-3,5-dioxopiperazin-1-yl]butane.hydrochloride Sample 8: Meso-2,3-bis[4-((S)-2-amino-3-(p-benzyloxyphenyl)propionyloxymethyl)-3,5-dioxopiperazin-1-yl]butane.hydrochloride Sample 9: Meso-2,3-bis[4-((S)-3-(p-acetoxyphenyl)-2-aminopropionyloxymethyl)-3,5-dioxopiperazin-1-yl]butane.hydrochloride Sample 10: Meso-2,3-bis[4-((S)-2-amino-4-carboxybutyryloxymethyl)-3,5-dioxopiperazin-1-yl]butane.hydrochloride Sample 11: Meso-2,3-bis[4-((S)-2-amino-4-benzyloxycarbonylbutyryloxymethyl)-3,5-dioxopiperazin-1-yl]butane.hydrochloride Sample 12: Meso-2,3-bis[4-((S)-2,6-diaminohexanoyloxymethyl)-3,5-dioxopiperazin-1-yl]butane.hydrobromide Sample 13: Meso-2,3-bis[4-((S)-2-amino-3-mercaptopropionyloxymethyl)-3,5-dioxopiperazin-1-yl]butane.trifluoroacetate Sample 14: Meso-2,3-bis[4-(2-pyrrolidinecarbonyloxymethyl)-3,5-dioxopiperazin-1-yl]butane.hydrochloride Sample 15: Meso-2,3-bis[4-(4-thiazolidinecarbonyloxymethyl)-3,5-dioxopiperazin-1-yl]butane.hydrochloride Sample 16: Erythro-2-[4-(2-aminoacetoxymethyl)-3,5-dioxopiperazin-1-yl]-3-(3,5-dioxopiperazin-1-yl)butane.trifluoroacetate Sample 17: Erythro-2-[4-((S)-2-aminopropionyloxymethyl)-3,5-dioxopiperazin-1-yl]-3-(3,5-dioxopiperazin-1-yl)butane.hydrochloride Sample 18: Erythro-2-[4-((S)-2-amino-4-methylvaleryloxymethyl)-3,5-dioxopiperazin-1-yl]-3-(3,5-dioxopiperazin-1-yl)butane.hydrochloride Sample 19: Erythro-2-[4-((S)-2-amino-3-(p-hydroxyphenyl)propionyloxymethyl)-3,5-dioxopiperazin-1-yl]-3-(3,5-dioxopiperazin-1-yl)butane.hydrochloride Sample 20: Erythro-2-[4-((S)-2-amino-3-carboxypropionyloxymethyl)-3,5-dioxopiperazin-1-yl]-3-(3,5-dioxopiperazin-1-yl)butane.hydrochloride Sample 21: Erythro-2-[4-((S)-2-amino-6-benzyloxycarbonylaminohexanoyloxymethyl)-3,5-dioxopiperazin-1-yl]-3-(3,5-dioxopiperazin-1-yl)butane.trifluoroacetate Comparative Compounds Sample A: 1,2-bis(4-isobutoxycarbonyloxymethyl-3,5-dioxopiperazin-1-yl)ethane Sample B: 1,2-bis[4-((R)-2-amino-2-phenylacetoxymethyl)-3,5-dioxopiperazin-1-yl]ethane.trifluoroacetate (Typical water soluble compound disclosed in Japanese Patent Publication (Kokai) No. 152660/1986)

I) Growth Inhibition of Tumor Cells of P388 Lymphocytic Leukemia in vitro:

Tumor cells were collected aseptically with capillary tube from ascites in DBA/2 male mice transplanted intraperitoneally with $1 \times 10^6$ cells of P388 lymphocytic leukemia 5 days before. Cell suspension was prepared at $5 \times 10^4$ cells/0.5 ml in a RPMI1640 medium supplemented with 10% fetal calf serum, kanamycin (0.1 mg/ml) and 2-hydroxyethyldisulfide (0.01 mM). Each test sample was dissolved or suspended in the medium at a concentration of from $2 \times 10^{-4}$ to $2 \times 10^{-10}$M.

A test tube involving 0.5 ml each of the cell suspension and the sample solution was kept for 48 hours at 37° C. for cultivation in the atmosphere containing 5% carbon dioxide. After the cultivation, the cells were counted by using of Coulter Counter and the inhibition of cell growth was calculated by the following formula:

$$\text{Growth Inhibition (\%)} = \left(1 - \frac{T}{C}\right) \times 100$$

T: number of cells in the culture containing test sample

C: number of cells in the culture of control

50% Inhibitory concentration of cell growth (IC$_{50}$) was calculated based on the inhibition in various concentrations of test compound and is shown in Table 1.

TABLE 1

| Sample | IC$_5$(M) |
| --- | --- |
| 1 | $4.8 \times 10^{-8}$ |
| 2 | $1.6 \times 10^{-8}$ |
| 3 | $5.8 \times 10^{-8}$ |
| 4 | $2.5 \times 10^{-8}$ |
| 5 | $1.8 \times 10^{-9}$ |
| 6 | $2.3 \times 10^{-8}$ |
| 7 | $1.9 \times 10^{-8}$ |
| 8 | $1.4 \times 10^{-9}$ |
| 9 | $9.4 \times 10^{-9}$ |
| 10 | $4.6 \times 10^{-8}$ |
| 11 | $1.4 \times 10^{-8}$ |
| 12 | $8.2 \times 10^{-9}$ |
| 13 | $4.7 \times 10^{-8}$ |
| 14 | $1.8 \times 10^{-8}$ |
| 15 | $6.5 \times 10^{-9}$ |
| 16 | $3.4 \times 10^{-8}$ |
| 17 | $4.1 \times 10^{-8}$ |
| 18 | $3.2 \times 10^{-8}$ |
| 19 | $1.7 \times 10^{-8}$ |
| 20 | $1.6 \times 10^{-8}$ |
| 21 | $3.8 \times 10^{-9}$ |
| A | $4.8 \times 10^{-5}$ |
| B | $3.0 \times 10^{-5}$ |

II) Increase in Life Span on L1210 Lymphoid Leukemia Tumor-transplanted Mouse:

The treated group to which the test sample was administered consisted of seven mice, while the control group consisted of ten mice. Six weeks old male mice (CDF$_1$, 25±2 g of body weight) were employed as host animals.

Tumor cells ($1.0 \times 10^6$) of L1210 lymphoid leukemia were transplanted subcutaneously into each mouse. The treatment was effected for 5 days from one day after the transplantation by administering prescribed dose of each test sample dissolved in physiological saline solution intravenously to the mice.

Antitumor activity of the test sample was evaluated by the rate of increase in life span (ILS) which was calculated with the following formula.

$$ILS (\%) = \left(\frac{T'}{C'} - 1\right) \times 100$$

T': median survival time of treated mice
C': median survival time of control mice
The results obtained are shown in Table 2.

TABLE 2

| Sample | Daily Dose (mg/kg) | ILS (%) |
|---|---|---|
| 2 | 16 | 105 |
| 3 | 17 | 126 |
| 4 | 18 | 154 |
| 5 | 20 | 157 |
| 7 | 24 | 138 |
| 8 | 26 | 123 |
| 10 | 19 | 84 |
| 11 | 24 | 138 |
| 14 | 17 | 113 |
| 15 | 18 | 108 |
| 18 | 13 | 120 |
| 19 | 15 | 95 |
| B | 20 | 20 |

The above results of the tests revealed that the compounds of the present invention exhibit remarkably strong antitumor activity in comparison with the known water soluble bis-dioxopiperazine derivative (comparative compound B).

The acute toxicity of the compounds of the present invention was examined by the following single administration test.

The test group to which the compound of the present invention was administered consisted of seven mice. Six weeks old male mice ($CDF_1$, 25±2 g of body weight) were employed as test animals.

These animals were intravenously give the test compound which was dissolved in the physiological saline solution and were observed for 14 days successively, and numbers of the mice died was determined.

The results are shown in Table 3.

TABLE 3

| Sample | Dose (mg/kg) | Numbers died |
|---|---|---|
| 3 | 87 | 2 |
| 5 | 75 | 2 |

The following descriptions are given for the administration routes, pharmaceutical forms and doses when bis-dioxopiperazine derivatives of the present invention are applied to human.

The compounds of the present invention may be administered orally in forms such as tablets, coated tablets, powders, granules, capsules, microcapsules, syrups and so on. They may be also administered parenterally in forms such as injections which may include dissolvable freeze-drying form, suppositories and so on.

In the preparation of these forms, pharmaceutically acceptable diluent bases, binders, disintegrators, lubricants, suspensions, emulsifiers, antiseptics, stabilizers and dispersing agents, for example, lactose, sucrose, starch, dextrin, crystalline cellulose, kaolin, calcium carbonate, talc, magnesium stearate, distilled water and physiological saline solution may be used.

Although the daily doses of these compounds may be varied according to the conditions, ages and weights of the subjects to be treated, the daily doses to adult humans may normally fall within the range of 1 to 600 mg, preferably 5 to 100 mg, and may be divided into two or three portions.

BEST MODE FOR CARRYING OUT THE INVENTION

PREPARATION AND EXAMPLES

The present invention is illustrated by the following preparation and examples, but it is to be noted that the present invention is not limited to the examples.

Production

Meso-2,3-bis(4-hydroxymethyl-3,5-dioxopiperazin-1-yl)butane

A mixture of meso-2,3-bis(3,5-dioxopiperazin-1-yl)butane (2.7 g, 10 mmol) and DMF (30 ml) was heated at 110° C. for 10 minutes. To the mixture, 37% aqueous formaldehyde solution (2.2 ml) was added, and then the mixture was heated at 140° C. with stirring for 1.5 hours. The reaction mixture was condensed under reduced pressure and the residue was treated with absolute ethanol. The resulting precipitates were collected by filtration and dried over calcium chloride to give 2.8 g (yield: 86%) of the titled compounds.

Melting Point: 299°–301° C. IR Spectrum $(KBr)cm^{-1}$: 1670, 1730 (C=O) NMR Spectrum $(DMSO-d_6)$ δppm: 0.89(6H,d,J=4 Hz) 2.77(2H,m) 3.37 and 3.47(8H,AB,J=17 Hz) 5.01(4H,d,J=7 Hz) 6.19(2H,t,J=7 Hz)

Example 1

Meso-2,3-bis[4-((S)-3-(p-benzyloxyphenyl)-2-N-tert-butoxycarbonylaminopropionyloxymethyl)-3,5-dioxopiperazin-1-yl]butane To a mixture of N-tert-butoxycarbonyl-O-benzyl-L-tyrosine (357 mg, 0.96 mmol) and anhydrous dichloromethane (10 ml), N,N'-carbonyldiimidazole (156 mg, 0.96 mmol) and methyl iodide (0.14 ml, 2.2 mmol) was added successively with stirring at room temperature. Then, the mixture was further stirred at room temperature for 1.5 hours. Meso-2,3-bis(4-hydroxymethyl-3,5-dioxopiperazin-1-yl)butane (137 mg, 0.4 mmol) was added to the mixture. After stirred for 16 hours at room temperature, the reaction mixture was condensed under reduced pressure and the residue was extracted with dichloromethane. The extract Was washed with 1N-hydrochloric acid and water, successively, and dried over magnesium sulfate. The extract was condensed under reduced pressure and the resulting residue was purified by column chromatography on silica gel, using chloroform-metanol (20:1) as an eluant to give 215 mg (yield: 51%) of the titled compound as white solid.

Melting Point: 161°–163° C. IR Spectrum $(KBr)cm^{-1}$: 1700, 1750 (C=O)

In accordance with the procedure of the Example 1, the following compounds were obtained from the corresponding starting materials.

Meso-2,3-bis[4-((S)-2-N-tert-butoxycarbonylaminoisovaleryloxymethyl)-3,5-dioxopiperazin-1-yl]butane Yield: 60% Melting Point: 128°–131° C. (dec.) IR Spectrum $(KBr)cm^{-1}$: 1700, 1750 (C=O)

Meso-2,3-bis[4-((S)-2-N-benzyloxycarbonylamino-4,4-dimethylvaleryloxymethyl-3,5-dioxopiperazin-1-yl]butane Yield: 58% Melting Point: 103°–106° C. (dec.) IR Spectrum $(KBr)cm^{-1}$: 1700, 1740 (C=O)

Meso-2,3-bis[4-((S)-2-N-tert-butoxycarbonylamino-3-phenylpropionyloxymethyl)-3,5-dioxopiperazin-1-yl]butane Yield: 52% Melting Point: 163.5°–165.5° C. (dec.) IR Spectrum (KBr)cm$^{-1}$: 1700, 1750 (C=O)

Meso-2,3-bis[4-((S)-2-N-tert-butoxycarbonylamino-3-(p-trifluoromethylphenyl)propionyloxymethyl)-3,5-dioxopiperazin-1-yl]butane Yield: 46% Melting Point: 191°–193° C. (dec.) IR Spectrum (KBr)cm$^{-1}$: 1700, 1750 (C=O)

Meso-2,3-bis[4-((S)-4-benzyloxycarbonyl-2-N-tert-butoxycarbonylaminobutyryloxymethyl)-3,5-dioxopiperazin-1-yl]butane Yield: 60% Melting Point: 90°–92° C. (dec.) IR Spectrum (KBr)cm$^{-1}$: 1700, 1750 (C=O)

Meso-2,3-bis[4-((S)-2-N-tert-butoxycarbonylamino-3-(p-methoxybenzylthio)propionyloxymethyl)-3,5-dioxopiperazin-1-yl]butane Yield: 59% Melting Point: 129°–131° C. (dec.) IR Spectrum (KBr)cm$^{-1}$: 1700, 1750 (C=O)

Meso-2,3-bis[4-(N-tert-butoxycarbonyl-2-pyrrolidinecarbonyloxymethyl)-3,5-dioxopiperazin-1-yl]butane Yield: 58% Melting Point: 79°–82° C. (dec.) IR Spectrum (KBr)cm$^{-1}$: 1700, 1750 (C=O)

Example 2

Meso-2,3-bis[4-((S)-2-N-tert-butoxycarbonylaminopropionyloxymethyl)-3,5-dioxopiperazin-1-yl]butane and erythro-2-[4-((S)-2-N-tert-butoxycarbonylaminopropionyloxymethyl)-3,5-dioxopiperazin-1-yl]-3-(3,5-dioxopiperazin-1-yl)butane In accordance with the procedure described in Example 1, 181 mg (0.96 mmol) of N-tert-butoxycarbonyl-L-alanine, 156 mg (0.96 mmol) of N,N′-carbonyldiimidazole, 0.14 ml (2.2 mmol) of methyl iodide and 274 mg (0.8 mmol) of meso-2,3-bis(4-hydroxymethyl-3,5-dioxopiperazin-1-yl)butane gave the titled compound which was purified by column chromatography on silica gel, using ethyl acetate and n-hexane (6:4) as an eluant.

Meso-2,3-bis[4-((S)-2-N-tert-butoxycarbonylaminopropionyloxymethyl)-3,5-dioxopiperazin-1-yl]butane Yield: 175 mg, 32% Melting Point: 177.5°–179° C. (dec.) IR Spectrum (KBr)cm$^{-1}$: 1700, 1710, 1750 (C=O)

Erythro-2-[4-((S)-2-N-tert-butoxycarbonylaminopropionyloxymethyl)-3,5-dioxopiperazin-1-yl]-3-(3,5-dioxopiperazin-1-yl)butane Yield: 182 mg, 47% Melting Point: 179°–180° C. (dec.) IR Spectrum (KBr)cm$^{-1}$: 1700, 1740 (C=O)

In accordance with the procedure of the Example 2, the following compounds were obtained from the corresponding starting materials.

Meso-2,3-bis[4-(2-N-tert-butoxycarbonylaminoacetoxymethyl)-3,5-dioxopiperazin-1-yl]butane Yield: 26% Melting Point: 199°–201° C. (dec.) IR Spectrum (KBr)cm$^{-1}$: 1700, 1750 (C=O)

Meso-2,3-bis[4-((S)-2-N-benzyloxycarbonylamino-4-methylvaleryloxymethyl)-3,5-dioxopiperazin-1-yl]butane Yield: 29% Melting Point: 134°–136° C. (dec.) IR Spectrum (KBr)cm$^{-1}$: 1700, 1750 (C=O)

Meso-2,3-bis[4-((S)-3-benzyloxycarbonyl-2-N-tert-butoxycarbonylaminopropionyloxymethyl)-3,5-dioxopiperazin-1-yl]butane Yield: 28% Melting Point: 83°–85.5° C. (dec.) IR Spectrum (KBr)cm$^{-1}$: 1700, 1750 (C=O)

Meso-2,3-bis[4-((S)-6-N-benzyloxycarbonylamino-2-N-tert-butoxycarbonylaminohexanoyloxymethyl)-3,5-dioxopiperazin-1-yl]butane Yield: 20% Melting Point: 123°–128° C. (dec.) IR Spectrum (KBr)cm$^{-1}$: 1700, 1750(C=O)

Meso-2,3-bis[4-(N-tert-butoxycarbonyl-4-thiazolidinecarbonyloxymethyl)-3,5-dioxopiperazin-1-yl]butane Yield: 22% Melting Point: 94°–97° C. (dec.) IR Spectrum (KBr)cm$^{-1}$: 1700, 1750 (C=O)

Erythro-2-[4-(2-N-tert-butoxycarbonylaminoacetoxymethyl)-3,5-dioxopiperazin-1-yl]-3-(3,5-dioxopiperazin-1-yl)butane Yield: 44% Melting Point: 189°–193° C. (dec.) IR Spectrum (KBr)cm$^{-1}$: 1700, 1750 (C=O)

Erythro-2-[4-((S)-2-N-benzyloxycarbonylamino-4-methylvaleryloxymethyl)-3,5-dioxopiperazin-1-yl]-3-(3,5-dioxopiperazin-1-yl)butane Yield: 38% Melting Point: 94°–95° C. (dec.) IR Spectrum (KBr)cm$^{-1}$: 1700, 1750 (C=O)

Erythro-2-[4-((S)-3-benzyloxycarbonyl-2-N-tert-butoxycarbonylaminopropionyloxymethyl)-3,5-dioxopiperazin-1-yl]-3-(3,5-dioxopiperazin-1-yl)butane Yield: 44% Melting Point: 114°–116° C. (dec.) IR Spectrum (KBr)cm$^{-1}$: 1700, 1740, 1760 (C=O)

Erythro-2-[4-((S)-6-N-benzyloxycarbonylamino-2-N-tert-butoxycarbonylaminohexanoyloxymethyl)-3,5-dioxopiperazin-1-yl]-3-(3,5-dioxopiperazin-1-yl)butane Yield: 43% Melting Point: 119°–124° C. (dec.) IR Spectrum (KBr)cm$^{-1}$: 1700, 1750 (C=O)

Erythro-2-[4-(N-tert-butoxycarbonyl-4-thiazolidinecarbonyloxymethyl)-3,5-dioxopiperazin-1-yl]-3-(3,5-dioxopiperazin-1-yl)butane Yield: 48% Melting Point: 157°–160° C. (dec.) IR Spectrum (KBr)cm$^{-1}$: 1700, 1750 (C=O)

Example 3

Meso-2,3-bis[4-((S)-2-N-tert-butoxycarbonylamino-3-(p-hydroxyphenyl)propionyloxymethyl)-3,5-dioxopiperazin-1-yl]butane One hundred milligram (0.1 mmol) of meso-2,3-bis[4-((S)-3-(p-benzyloxyphenyl)-2-N-tert-butoxycarbonylaminopropionyloxymethyl)-3,5-dioxopiperazin-1-yl]-butane was added to 40 ml of a mixed solvent of ethyl acetate and ethanol (1:1). To the mixture, 60 mg of 10% palladium on carbon was added as catalyst and the mixture was stirred for 16 hours under hydrogen. The catalyst was removed by filtration from the reaction mixture and the filtrate was condensed under reduced pressure and the resulting residue was purified by column chromatography on silica gel, using chloroform-methanol (20:1) as an eluant to give 80 mg (yield: 52%) of the titled compound as white solid.

Melting Point: 99°–103° C. IR Spectrum (KBr)cm$^{-1}$: 1700, 1750 (C=O)

In accordance with the procedure of the Example 3, the following compounds were obtained from the corresponding starting materials.

Meso-2,3-bis[4-((S)-2-N-tert-butoxycarbonylamino-3-carboxypropionyloxymethyl-3,5-dioxopiperazin-1-yl]butane Yield: 92% Melting Point: 89°–91° C. (dec.) IR Spectrum (KBr)cm$^{-1}$: 1700, 1750 (C=O)

Meso-2,3-bis[4-((S)-2-N-tert-butoxycarbonylamino-4-carboxybutyryloxymethyl)-3,5-dioxopiperazin-1-yl]butane Yield: 92% Melting Point: 140°–143° C. (dec.) IR Spectrum (KBr)cm$^{-1}$: 1710, 1750 (C=O)

Example 4

Meso-2,3-bis[4-((S)-2-amino-3-(p-hydroxyphenyl)propionyloxymethyl)-3,5-dioxopiperazin-1-yl]butane.hydrochloride Fifty milligram (0.06 mmol) of meso-2,3-bis[4-((S)-2-N-tertbutoxycarbonylamino-3-(p-hydroxyphenyl)propionyloxymethyl)-3,5-dioxopiperazin-1-yl]butane was added to 5 ml of dioxane dissolved with hydrogen chloride (4N) at 0° C. and stirred at 0° C. for 1 hour and was further stirred at room temperature for 1 hour. The reaction mixture was condensed under reduced pressure, treated with anhydrous ether and stirred at room temperature for 1 hour. The resulting precipitates were collected by filtration and dried over potassium hydroxide under reduced pressure to give 16 mg (yield: 33%) of the titled compound as light yellow powder.

Melting Point: 171°–175° C. (dec.) IR Spectrum (KBr)cm$^{-1}$: 1700, 1750 (C=O) NMR Spectrum (D$_2$O) δppm: 1.0–1.1(6H,m) 2.9–3.0(2H,m) 3.1–3.2(4H,m) 3.6–3.8(8H,m) 4.3–4.4(2H,m) 5.66(2H,d,J=10 Hz) 6.00(2H,d,J=10 Hz) 6.84 (4H,d,J=8 Hz) 7.09 (4H,d,J=8 Hz)

In accordance with the procedure of the Example 4, the following compounds were obtained from the corresponding starting materials.

Meso-2,3-bis[4-(2-aminoacetoxymethyl)-3,5-dioxopiperazin-1-yl]butane.hydrochloride Melting Point: 127°–134° C. (dec.) IR Spectrum (KBr)cm$^{-1}$: 1700, 1750, 1770 (C=O) NMR Spectrum (D$_2$O) δppm: 1.21(6H,d,J=6 Hz) 3.1–3.2(2H,m) 3.86 and 3.94(8H,AB,J=17 Hz) 3.94(4H,s) 5.91(4H,s)

Meso-2,3-bis[4-((S)-2-aminopropionyloxymethyl)-3,5-dioxopiperazin-1-yl]butane.hydrochloride Melting Point: 69°–74° C. (dec.) IR Spectrum (KBr)cm$^{-1}$: 1710, 1760 (C=O) NMR Spectrum (D$_2$O) δppm: 1.2–1.3(6H,m) 1.53(6H,d,J=7 Hz) 3.3–3.4(2H,m) 3.94 and 4.01(8H,AB,J=15 Hz) 4.22(2H,q,J=7 Hz) 5.93(4H,s)

Meso-2,3-bis[4-((S)-2-aminoisovaleryloxymethyl)-3,5-dioxopiperazin-1-yl]butane.hydrochloride Melting Point: 82°–86° C. (dec.) IR Spectrum (KBr)cm$^{-1}$: 1710, 1760 (C=O) NMR Spectrum (D$_2$O) δppm: 0.9–1.0(12H,m) 1.18(6H,d,J=5 Hz) 2.3–2.4(2H,m) 3.0–3.1(2H,m) 3.83 and 3.91(8H,AB,J=17 Hz) 4.06(2H,d,J=4 Hz) 5.98 and 6.00(4H,AB,J=10 Hz)

Meso-2,3-bis[4-((S)-2-amino-3-phenylpropionyloxymethyl)-3,5-dioxopiperazin-1-yl]butane.hydrochloride Melting Point: 173°–176° C. (dec.) IR Spectrum (KBr)cm$^{-1}$: 1710, 1760 (C=O) NMR Spectrum (D$_2$O) δppm: 1.1(6H,m) 2.8(2H,m) 3.23(2H,d,J=3 Hz) 3.25(2H,d,J=3 Hz) 3.7–3.9(8H,m) 4.4–4.5(2H,m) 5.7–5.8(2H,m) 5.9–6.0(2H,m) 7.2–7.4(10H,m)

Meso-2,3-bis[4-((S)-2-amino-3-(p-trifluoromethylphenyl)propionyloxymethyl)-3,5-dioxopiperazin-1-yl]butane.hydrochloride Melting Point: 143°–147° C. (dec.) IR Spectrum (KBr)cm$^{-1}$: 1700, 1750 (C=O) NMR Spectrum (D$_2$O) δppm: 1.0–1.1(6H,m) 2.8–3.0(2H,m) 3.2–3.5(4H,m) 3.64 and 3.74(8H,AB,J=19 Hz) 4.52(2H,q,J=8 Hz) 5.76(2H,d,J=10 Hz) 5.98(2H,d,J=10 Hz) 7.42(4H,d,J=8 Hz) 7.69 (4H,d, J=8 Hz)

Meso-2,3-bis[4-((S)-2-amino-3-(p-benzyloxyphenyl)propionyloxymethyl)-3,5-dioxopiperazin-1-yl]butane.hydrochloride Melting Point: 114°–119° C. (dec.) IR Spectrum (KBr)cm$^{-1}$: 1700, 1750 (C=O) NMR Spectrum (D$_2$O) δppm: 0.7–0.9(6H,m) 2.4–2.6(2H,m) 3.2–3.4(12H,m) 4.3–4.4(2H,m) 5.5–5.7(2H,m) 5.8–6.0(2H,m) 6.8–6.9(4H,m) 7.0–7.4(14H,m)

Meso-2,3-bis[4-((S)-2-amino-3-carboxypropionyloxymethyl)-3,5-dioxopiperazin-1-yl]butane.hydrochloride Melting Point: 108°–112° C. (dec.) IR Spectrum (KBr)cm$^{-1}$: 1700, 1750 (C=O) NMR Spectrum (D$_2$O) δppm: 1.2–1.3(6H,m) 3.0–3.3(4H,m) 3.3–3.4(2H,m) 3.94 and 4.04(8H,AB,J=17 Hz) 4.50(2H,t,J=6 Hz) 5.85(2H,d,J=10 Hz) 6.03(2H,d,J=10 Hz)

Meso-2,3-bis[4-((S)-2-amino-4-carboxybutyryloxymethyl)-3,5-dioxopiperazin-1-yl]butane.hydrochloride Melting Point: 127° C. (dec.) IR Spectrum (KBr)cm$^{-1}$: 1705, 1750 (C=O) NMR Spectrum (D$_2$O) δppm: 1.10(6H,d,J=6 Hz) 2.18 and 2.20(4H,AB,J=7 Hz) 2.5–2.7(4H,m) 2.9–3.0(2H,m) 3.68 and 3.77(8H,AB,J=17 Hz) 4.24(2H,t,J=7 Hz) 5.85 and 5.99(4H,AB,J=10 Hz)

Meso-2,3-bis[4-((S)-2-amino-3-benzyloxycarbonylpropionyloxymethyl)-3,5-dioxopiperazin-1-yl]butane.hydrochloride Melting Point: 60°–64° C. (dec.) IR Spectrum (KBr)cm$^{-1}$: 1700, 1750 (C=O) NMR Spectrum (D$_2$O) δppm: 0.93(3H,d,J=6 Hz) 0.96(3H,d,J=6 Hz) 2.6–2.8(2H,m) 3.0–3.2(4H,m) 3.56 and 3.63(8H,AB,J=18 Hz) 4.4–4.6(2H,m) 5.19(4H,s) 5.75(2H,d,J=10 Hz) 5.94(2H,d,J=10 Hz) 7.44(10H,s)

Meso-2,3-bis[4-((S)-2-amino-4-benzyloxycarbonyl-butyryloxymethyl)-3,5-dioxopiperazin-1-yl]butane.hydrochloride Melting Point: 132°–136° C. (dec.) IR Spectrum (KBr)cm$^{-1}$: 1705, 1750 (C=O) NMR Spectrum (D$_2$O) δppm: 0.87(6H,d,J=5 Hz) 2.1–2.3(4H,m) 2.5–2.7(6H,m) 3.3–3.6(8H,m) 4.21(2H,t,J=5 Hz) 5.16(4H,s) 5.7–6.1(4H,m) 7.42(10H,s)

Meso-2,3-bis[4-(2-pyrrolidinecarbonyloxymethyl)-3,5-dioxopiperazin-1-yl]butane.hydrochloride Melting Point: 110°–115° C. (dec.) IR Spectrum (KBr)cm$^{-1}$: 1700, 1750 (C=O) NMR Spectrum (D$_2$O) δppm: 1.21(6H,d,J=5 Hz) 2.0–2.2(6H,m) 2.3–2.5(2H,m) 3.1–3.2(2H,m) 3.4–3.5(4H,m) 3.86 and 3.94(8H,AB,J=17 Hz) 4.4–4.5(2H,m) 5.91 and 5.93(4H,AB,J=5 Hz)

Meso-2,3-bis[4-(4-thiazolidinecarbonyloxymethyl)-3,5-dioxopiperazin-1-yl]butane.hydrochloride Melting Point: 161°–166° C. (dec.) IR Spectrum (KBr)cm$^{-1}$: 1700, 1750 (C=O) NMR Spectrum (D$_2$O) δppm: 1.17(6H,d,J=5 Hz) 3.0–3.1(2H,m) 3.4–3.6(4H,m) 3.79 and 3.89(8H,AB,J=17 Hz) 4.44 and 4.50(4H,AB,J=10 Hz) 4.9–5.0(2H,m) 5.92 and 5.98(4H,AB,J=10 Hz)

Erythro-2-[4-((S)-2-aminopropionyloxymethyl)-3,5-dioxopiperazin-1-yl]-3-(3,5-dioxopiperazin-1-yl)butane.-hydrochloride Melting Point: 145°–149° C. (dec.) IR Spectrum (KBr)cm$^{-1}$: 1700, 1720, 1750 (C=O) NMR Spectrum (D$_2$O) δppm: 1.28(3H,d,J=7 Hz) 1.45(3H,d,J=7 Hz) 1.57(3H,d,J=7 Hz) 3.4–3.5(1H,m) 3.6–3.7(1H,m) 3.82 and 3.94(4H,AB,J=17 Hz) 4.15 and 4.23(4H,AB,J=16 Hz) 4.22(1H,q,J=7 Hz) 5.92(2H,s)

Erythro-2-[4-(4-thiazolidinecarbonyloxymethyl)-3,5-dioxopiperazin-1-yl]-3-(3,5-dioxopiperazin-1-yl)butane.-hydrochloride Melting point: 140°–145° C. (dec.) IR Spectrum (KBr)cm$^{-1}$: 1700, 1750 (C=O) NMR Spectrum (D$_2$O) δppm: 1.18(3H,d,J=7 Hz) 1.30(3H,d,J=7 Hz) 3.1–3.2(1H,m) 3.3–3.4(1H,m) 3.4–3.5(2H,m) 3.76 and 3.84(4H,AB,J=15 Hz) 3.88 and 3.98(4H,AB,J=17 Hz) 4.44 and 4.50(2H,AB,J=10 Hz) 4.9–5.0(1H,m) 5.92 and 5.97(2H,AB,J=10 Hz)

Example 5

Meso-2,3-bis[4-((S)-2-amino-3-mercaptopropionyloxymethyl)-3,5-dioxopiperazin-1-yl]butane.trifluoroacetate To 5 ml (65 mmol) of trifluoroacetic acid was added a mixture of 0.1 ml (0.92 mmol) of anisole and 38 mg (0.04 mmol) of meso-2,3-bis[4-((S)-2-N-tert-butoxycarbonylamino-3-(p-methoxybenzylthio)propionyloxymethyl)-3,5-dioxopiperazin-1-yl]butane successively and the mixture was refluxed for 4 hours. The reaction mixture was condensed under reduced pressure and the residue was treated with anhydrous ether. Then, the resulting precipitates were collected by filtration. The precipitates were added to 5 ml of water, and the insoluble matter in the solution was filtered off. The filtrate was freeze-dried to give 21 mg (yield: 70%) of the titled compound as light yellow powder.

Melting Point: 59°–62° C. (dec.) IR Spectrum (KBr)cm$^{-1}$: 1670, 1700, 1750 (C=O) NMR Spectrum (D$_2$O) δppm: 1.0–1.1(6H,m) 2.8–3.0(2H,m) 3.0–3.2(4H,m) 3.64 and 3.74(8H,AB,J=17 Hz) 4.4–4.5(2H,m) 5.86(2H,d,J=10 Hz) 6.01(2H,d,J=10 Hz)

In accordance with the procedure of the Example 5, the following compounds were obtained from the corresponding starting materials.

Erythro-2-[4-(2-aminoacetoxymethyl)-3,5-dioxopiperazin-1-yl]-3-(3,5-dioxopiperazin-1-yl)butane.trifluoroacetate Yield: 44% Melting Point: 160°–166° C. (dec.) IR Spectrum (KBr)cm$^{-1}$: 1700, 1750 (C=O) NMR Spectrum (D$_2$O) δppm: 1.20(6H,d,J=5 Hz) 3.1–3.2(2H,m) 3.83 and 3.91(8H,AB,J=16 Hz) 3.93(2H,s) 5.90(2H,s)

Erythro-2-[4-((S)-2-amino-6-N-benzyloxycarbonylaminohexanoyloxymethyl)-3,5-dioxopiperazin-1-yl]-3-(3,5-dioxopiperazin-1-yl)butane.trifluoroacetate Yield: 74% Melting Point: 168°–173° C. (dec.) IR Spectrum (KBr)cm$^{-1}$: 1700, 1750 (C=O) NMR Spectrum (D$_2$O) δppm: 0.9–1.1(6H,m) 1.2–1.5(4H,m) 1.8–2.0(2H,m) 2.7–2.8(2H,m) 3.0–3.1(2H,m) 3.3–3.7(8H,m) 4.0–4.2(1H,m) 5.11(2H,s) 5.78(1H,d,J=8 Hz) 5.99(1H,d,J=9 Hz) 7.41(5H,s)

Example 6

Meso-2,3-bis[4-((S)-2,6-diaminohexanoyloxymethyl)-3,5-dioxopiperazin-1-yl]butane.hydrobromide Thirty milligram (0.03 mmol) of meso-2,3-bis[4-((S)-6-N-benzyloxycarbonylamino-2-N-tert-butoxycarbonylaminohexanoyloxymethyl)- 3,5-dioxopiperazin-1-yl]butane was added to 5 ml of acetic acid containing hydrogen bromide (30%) at 0° C. and stirred at the same temperature for 1 hour and further stirred at room temperature for 1 hour. The reaction mixture was condensed under reduced pressure and the residue was treated with anhydrous ether and stirred for 1 hour. The resulting precipitates were collected by filtration and dried over potassium hydroxide under reduced pressure to give 14 mg (yield: 52%) of the titled compound as light yellow powder.

Melting Point: 170°–176° C. (dec.) IR Spectrum (KBr)cm$^{-1}$: 1700, 1750 (C=O) NMR Spectrum (D$_2$O) δppm: 1.19(6H,d,J=5 Hz) 1.4–1.5(4H,m) 1.6–1.8(4H,m) 1.9–2.0(4H,m) 2.9–3.0(4H,m) 3.1–3.2(2H,m) 3.84 and 3.91(8H,AB,J=17 Hz) 4.1–4.2(2H,m) 5.90 and 5.93(4H,AB,J=5 Hz)

Example 7

Meso-2,3-bis[4-((S)-3-(p-acetoxyphenyl)-2-aminopropionyloxomethyl)-3,5-dioxopiperazin-1-yl]butane.hydrochloride Two milliliter of acetic anhydride was added to anhydrous pyridine solution (10 ml) of 70 mg (0.08 mmol) of meso-2,3-bis[4-((S)-2-N-tert-butoxycarbonylamino-3-(p-hydroxyphenyl)propionyloxymethyl)-3,5-dioxopiperazin-1-yl]butane with stirring at room temperature and further stirred at room temperature for 16 hours. The reaction mixture was condensed under reduced pressure and the residue was treated with anhydrous ether and stirred at room temperature for 1 hour. The resulting precipitates were collected by filtration and dried over particles of potassium hydroxide under reduced pressure to give 64 mg (yield: 83%) of meso-2,3- bis[4-((S)-3-(p-acetoxyphenyl)-2-N-tert-butoxycarbonylaminopropionyloxymethyl)-3,5-dioxopiperazin-1-yl]butane. Then, according to a similar procedure described in Example 4, 44 mg (yield: 85%) of the titled compound was obtained as light yellow powder from 60 mg (0.06 mmol) of the preceding products.

Melting Point: 162°–167° C. (dec.) IR Spectrum (KBr)cm$^{-1}$: 1700, 1750 (C=O) NMR Spectrum (D$_2$O) δppm: 1.0–1.1(6H,m) 2.33(6H,s) 2.8–2.9(2H,m) 3.2–3.3(4H,m) 3.61 and 3.71(8H,AB,J=17 Hz) 4.4–4.5(2H,m) 5.73(2H,d,J=10 Hz) 5.99(2H,d,J=10 Hz) 7.12 and 7.28 (8H,AB, J=8 Hz)

Example 8

Erythro-2-[4-((S)-2-amino-3-carboxypropionyloxymethyl)-3,5-dioxopiperazin-1-yl]-3-(3,5-dioxopiperazin-1-yl)butane.hydrochloride According to the procedure described in Example 3, 83 mg (yield: 96%) of erythro-2-[4-((S)-2-N-tert-butoxycarbonylamino-3-carboxypropionyloxymethyl)-3,5-dioxopiperazin-1-yl]-3-(3,5-dioxopiperazin-1-yl)butane was obtained as white powder from 100 mg (0.16 mmol) of erythro-2-[4-(3-benzyloxycarbonyl-2-N-tert-butoxycarbonylaminopropionyloxymethyl)-3,5-dioxopiperazin-1-yl]-3-(3,5-dioxopiperazin-1-yl)butane. Then, according to a similar procedure described in Example 4, 20 mg (yield: 79%) of the titled compound was obtained as light yellow solid from 29 mg (0.06 mmol) of the compound thus obtained.

Melting Point: 112°–114° C. (dec.) IR Spectrum (KBr)cm$^{-1}$: 17,000,1740 (C=O) NMR Spectrum (D$_2$O) δppm: 1.26(3H,d J=7 Hz) 1.45 (3H,d,J=7 Hz) 3.0–3.3(2H,m) 3.4–3.5(1H,m) 3.6–3.7(1H,m) 3.83 and 3.89(4H,AB,J=15 Hz) 4.16 and 4.24(4H,AB,J=17 Hz) 4.50(1H,t,J=5 Hz) 5.77(1H,d,J=10 Hz) 6.05(1H,d,J=10 Hz)

Example 9

Erythro-2-[4-((S)-2-amino-3-(p-hydroxyphenyl)propionyloxymethyl)-3,5-dioxopiperazin-1-yl]-3-(3,5-dioxopiperazin-1-yl)butane.hydrochloride Meso-2,3-bis(4-hydroxymethyl-3,5-dioxopiperazin-1-yl) butane (206 mg 0.6 mmol) was treated with 268 mg (0.72 mmol) of N-tert-butoxycarbonyl-O-benzyl-L-tyrosine, 117 mg (0.72 mmol) of N,N'-carbonyldiimidazole and 0.11 ml (1.7 mmol) of methyl iodide by a similar procedure described in Example 1 to give 210 mg (yield: 52%, m.p. 86°–88° C.) of erythro-2-[4-((S)-3-(p-benzyloxyphenyl)-2-N-tert-butoxycarbonylaminopropionyloxymethyl)-3,5-dioxopiperazin-1-yl]-3-(3,5-dioxopiperazin-1-yl)butane as colorless powder.

According to the procedure described in Example 3, 74 mg (yield: 86%) of erythro-2-[4-((S)-2-N-tert-butoxycarbonylamino-3-(p-hydroxyphenyl)propionyloxymethyl)-3,5-dioxopiperazin-1-yl]-3-(3,5-dioxopiperazin-1-yl)butane was obtained as colorless powder from 100 mg (0.15 mmol) of the compound thus obtained. Then, according to a similar procedure described in Example 4, 54 mg (yield: 87%) of the titled compound was obtained as light yellow powder from 70 mg (0.12 mmol) of the preceding product.

Melting Point: 168°–173° C. (dec.) IR Spectrum (KBr)cm$^{-1}$: 1700, 1750 (C=O) NMR Spectrum (D$_2$O) δppm: 1.15 (3H,d,J=8 Hz) 1.25(3H,d,J=7 Hz) 3.1–3.3(2H,m) 3.71 and 3.77(4H,AB,J=11 Hz) 3.82 and 3.90(4H,AB,J=10 Hz) 4.4(1H,m) 5.72(1H,d,J=10 Hz) 5.98(1H,d,J=10 Hz) 6.86(2H,d,J=9 Hz) 7.12(2H,d,J=9 Hz)

Example 10

Meso-2,3-bis[4-((S)-2-amino-4,4-dimethylvaleryloxymethyl)-3,5-dioxopiperazin-1-yl]butane.hydrochloride To 10 ml of acetic acid was added 100 mg (0.12 mmol) of meso-2,3-bis[4-((S)-2-N-benzyloxycarbonylamino-4,4-dimethylvaleryloxymethyl)-3,5-dioxopiperazin-1-yl]butane and 25 mg of platinum oxide as a catalyst. The mixture was catalytically hydrogenated for 16 hours under hydrogen. The catalyst was removed from the reaction mixture by filtration and the filtrate was treated with 2 ml of a solution of dioxane containing hydrogen chloride (4N) and stirred for 1 hour. The mixture was condensed under reduced pressure and the obtained residue was added with anhydrous ether. The resulting precipitates were collected by filtration, added to 40 ml of water and freeze-dried to give 76 mg (yield: 98%) of the titled compound as light yellow powder.

Melting Point: 160°–165° C. (dec.) IR Spectrum (KBr)cm$^{-1}$: 1690, 1750 (C=O) NMR Spectrum (D$_2$O) δppm: 0.94(18H,s) 1.6–1.7(2H,m) 1.9–2.0(2H,m) 2.8(2H,m) 3.64 and 3.73(8H,AB,J=17 Hz) 4.1–4.2(2H,m) 5.86 and 5.97(4H,AB,J=10 Hz)

In accordance with the procedure of the Example 10, the following compounds were obtained from the corresponding starting materials.

Meso-2,3-bis[4-((S)-2-amino-4-methylvaleryloxymethyl)-3,5-dioxopiperazin-1-yl]butane.hydrochloride Melting Point: 120°–126° C. (dec.) IR Spectrum (KBr)cm$^{-1}$: 1706, 1758 (C=O) NMR Spectrum (D$_2$O) δppm: 0.92(12H,d,J=6 Hz) 1.1(6H,m) 1.4–1.9(6H,m) 2.9(2H,m) 3.66 and 3.76(8H,AB,J=18 Hz) 4.16(2H,t,J=6 Hz) 5.84 and 5.98(4H,AB,J=10 Hz)

Erythro-2-[4-((S)-2-amino-4-methylvaleryloxymethyl)-3,5-dioxopiperazin-1-yl]-3-(3,5-dioxopiperazin-1-yl)butane.hydrochloride Melting Point: 110°–115° C. (dec.) IR Spectrum (KBr)cm$^{-1}$: 1708, 1745 (C=O) NMR Spectrum (D$_2$O) δppm: 0.93(6H,d,J=6 Hz) 1.21(3H,d,J=6.5 Hz) 1.35(3H,d,J=7 Hz) 1.6–1.9(3H,m) 3.3(1H,m) 3.5(1H,m) 3.40 and 3.45(4H,AB,J=17 Hz) 3.87 and 3.97(4H,AB,J=17 Hz) 4.17(1H,t,J=7 Hz) 5.88 and 5.95 (2H, AB, J=11 Hz)

CAPABILITY OF EXPLOITATION IN INDUSTRY

As described above, the water soluble bis-dioxopiperazine derivatives according to the present invention are water soluble salts having excellent antitumor activity and may have expanded pharmaceutical forms of administration which enables wider clinical applicability.

It is claimed:

1. A pharmaceutically acceptable acid addition salt of a bis-dioxopiperazine derivative represented by the formula (I):

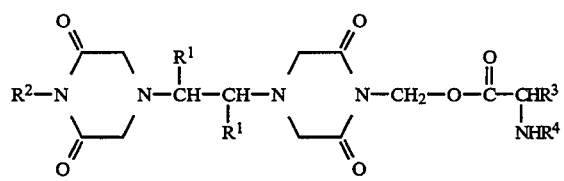

wherein $R^1$ represents a $C_{1-6}$ alkyl group,
$R^2$ represents a hydrogen atom or:

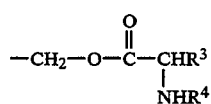

and $R^3$ is coupled with $R^4$ into a 5-membered saturated ring, which either contains no additional ring heteroatoms or contains one sulfur atom as an additional ring heteroatom.

2. The compound according to claim 1, wherein $R^1$ is methyl and $R^2$ is a group of the formula:

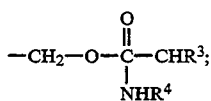

and $R^3$ and $R^4$ are coupled to form pyrrolidinyl or thiazolidinyl.

3. The compound according to claim 2, wherein $R^3$ and $R^4$ are coupled to form pyrrolidinyl.

4. The compound according to claim 2, wherein $R^3$ and $R^4$ are coupled to form thiazolidinyl.

5. The compound according to any one of claims 2 to 4, which is in a meso form.

6. The compound according to claim 1, wherein $R^1$ is methyl and $R^2$ is hydrogen, and $R^3$ and $R^4$ are coupled to form pyrrolidinyl or thiazolidinyl.

7. The compound according to claim 6, wherein $R^3$ and $R^4$ are coupled to form thiazolidinyl.

8. The compound according to any one of claims 6 or 7, which is in an erythro form.

9. A synthetic intermediate of a bis-dioxopiperazine derivative, represented by the formula (II):

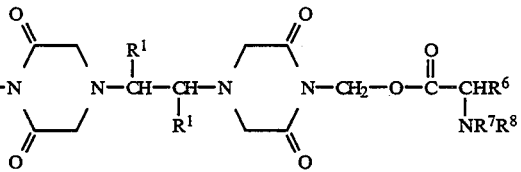

wherein $R^1$ represents a $C_{1-8}$ alkyl group,
$R^5$ represents a hydrogen atom or:

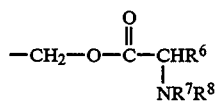

$R^6$ is coupled with $R^7$ into a 5-membered saturated ring, which may contain one sulfur atom as an additional ring heteroatom, and
$R^8$ represents a protecting group for the amino group.

10. The compound according to claim 9, wherein $R^1$ is methyl and $R^5$ is a group of the formula:

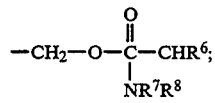

and $R^6$ and $R^7$ are coupled to form pyrrolidinyl or thiazolidinyl, and $R^8$ is tert-butoxycarbonyl or benzyloxycarbonyl.

11. The compound according to claim 10, wherein $R^6$ and $R^7$ are coupled to form pyrrolidinyl and $R^8$ is tert-butoxycarbonyl.

12. The compound according to claim 10, wherein $R^6$ and $R^7$ are coupled to form thiazolidinyl and $R^8$ is tert-butoxycarbonyl.

13. The compound according to any one of claims 10 to 12, which is in a meso form.

14. The compound according to claim 9, wherein $R^1$ is methyl and $R^5$ is hydrogen, and $R^6$ and $R^7$ are coupled to form pyrrolidinyl or thiazolidinyl, and $R^8$ is tert-butoxycarbonyl or benzyloxycarbonyl.

15. The compound according to claim 14, wherein $R^6$ and $R^7$ are coupled to form thiazolidinyl and $R^8$ is tert-butoxycarbonyl.

16. The compound according to any one of claims 14 or 15, which is in an erythro form.

* * * * *

UNITED STATES PATENT AND TRADEMARK OFFICE
CERTIFICATE OF CORRECTION

PATENT NO. : 5,393,889
DATED : February 28, 1995
INVENTOR(S) : Muneaki Takase, et al.

It is certified that error appears in the above-identified patent and that said Letters Patent is hereby corrected as shown below:

Column 1, Line 51 " 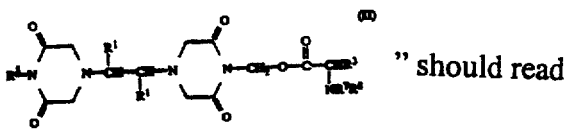 " should read

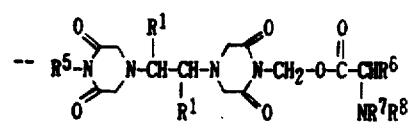 ···(II) --.

UNITED STATES PATENT AND TRADEMARK OFFICE
CERTIFICATE OF CORRECTION

PATENT NO. : 5,393,889
DATED : February 28, 1995
INVENTOR(S) : Muneaki Takase, et al.

It is certified that error appears in the above-identified patent and that said Letters Patent is hereby corrected as shown below:

Column 8, Line 22, "$IC_5(M)$" should read --$IC_{50}(M)$--.

Column 13, Line 32, "N-tertbutoxycarbonylamino" should read --N-tert-butoxycarbonylamino--.

Column 17, Line 32, "17,000," should read --1,700,--.

Column 20, Line 10, "$C_{1-8}$" should read --$C_{1-6}$--.

Signed and Sealed this

Twenty-ninth Day of June, 1999

Q. TODD DICKINSON

*Attest:*

*Attesting Officer*   Acting Commissioner of Patents and Trademarks